United States Patent [19]

Nauta

[11] 3,996,284
[45] Dec. 7, 1976

[54] NAPHTHYL AND TETRAHYDRONAPHTHYL DI-ETHERS

[76] Inventor: Wijbe Thomas Nauta, Rembrandtlaan 17, Nieuw Loosdrecht, Netherlands

[22] Filed: Apr. 10, 1974

[21] Appl. No.: 459,721

Related U.S. Application Data

[63] Continuation-in-part of Ser. No. 127,381, abandoned.

[52] U.S. Cl. .......................... 260/570.7; 260/348 R; 260/501.18; 260/612 D; 260/621 N; 260/623 R; 260/626 R; 424/316; 424/330
[51] Int. Cl.² ..................................... C07C 93/06
[58] Field of Search ............... 260/570.7, 501.18; 424/330

[56] References Cited

UNITED STATES PATENTS

| | | | |
|---|---|---|---|
| 3,033,640 | 5/1962 | Hofer et al. | 260/570.7 X |
| 3,337,628 | 8/1967 | Crowther et al. | 260/570.7 |
| 3,432,545 | 3/1969 | Horne | 260/570.7 X |

OTHER PUBLICATIONS

Kranz et al., "Chemical Abstracts", vol. 67, p. 6011, Section 64046k (1967).
Terentev et al., "Chemical Abstracts", vol. 57, pp. 16455–16456 (1962).

*Primary Examiner*—Robert V. Hines
*Attorney, Agent, or Firm*—Robert E. Burns; Emmanuel J. Lobato; Bruce L. Adams

[57] ABSTRACT

Naphthyl and tetrahydronaphthyl diethers of the formula

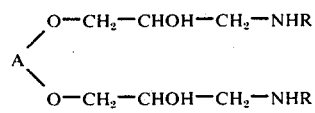

wherein A represents a naphthylene group or a 5,6,7,8-tetrahydronaphthylene group having their ether chains attached to the 1 and 2 or 2 and 3 positions or, when A represents a naphthylene group, to the 1 and 8 positions, which aromatic groups may also have substituted therein one to three substituents selected from halogen atoms, lower alkyl, lower alkenyl, benzyl, nitro and lower acyl groups, said substituents being present in the aromatic part in case A represents a 5,6,7,8-tetrahydronaphthylene group and R represents an isopropyl or tertiary butyl group, and acid addition salts thereof.

The compounds are useful anti-arrhythmic agents and also show local anaesthetic activity in mammals.

11 Claims, No Drawings

NAPHTHYL AND TETRAHYDRONAPHTHYL DI-ETHERS

This is a continuation-in-part of Ser. No. 127,381, and now abandoned, filed Mar. 23, 1971.

BRIEF DESCRIPTION OF THE INVENTION

This invention relates to new, therapeutically useful ethers and acid addition salts thereof, to processes for their preparation and to pharmaceutical compositions containing them.

The new ethers of the invention are the naphthyl and tetrahydronaphthyl di-ethers of the general formula

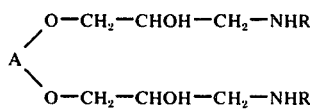   I wherein A represents a naphthylene group or a 5,6,7,8-tetrahydronaphthylene group having their ether chains attached to the 1 and 2 or 2 and 3 positions or, when A represents a naphthylene group, to the 1 and 8 positions, which aromatic groups may also have substituted therein one to three substituents selected from halogen atoms, lower alkyl, lower alkenyl, benzyl, nitro and lower acyl groups, said substituents being present in the aromatic part in case A represents a 5,6,7,8-tetrahydronaphthylene group and R represents an isopropyl or tertiary butyl group, and acid addition salts thereof.

The term "lower" as applied herein to alkyl, alkenyl and acyl groups indicates that the group contains a straight or branched hydrocarbon chain with at most 6 carbon atoms. Preferred compounds are those in which the group A is unsubstituted.

The naphthyl and tetrahydronaphthyl di-ethers of formula I have valuable therapeutic properties. For use as therapeutics they have pronounced anti-arrhythmic properties and, in addition, show local anaesthetic activities. They have only a weak β-sympatholytic activity. The compounds of formula I may be used as bases or as acid addition salts containing pharmaceutically acceptable non-toxic anions e.g. the hydrohalides, sulphates, oxalates, tartrates, fumarates, acetates, citrates, maleates, succinates, lactates and pamoates. The bases or non-toxic acid addition salts thereof may be administered orally or parenterally in a pharmacologically acceptable carrier according to accepted pharmaceutical practice. The dosage will depend on the mammalian species treated. For application an antiarrhythmics in adult humans the oral dosage will be from 5 to 100 mg. daily.

According to a feature of the invention the naphthyl and tetrahydronaphthyl di-ethers of formula I are prepared by reacting a di(chlorohydrin) ether of the formula:

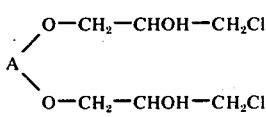   II wherein A is as hereinbefore defined, with an amine of the formula $NH_2R$, wherein R is as hereinbefore defined. The reaction is preferably carried out in an inert organic solvent, such as benzene, toluene or an alcohol (e.g. ethanol). The reaction temperature may range from room temperature to 120° C. and the reaction time from 3 to 30 hours. The best yields are obtained by heating the reactants in benzene in a closed vessel, e.g. a Carius tube, for 20 hours at 80° C. with a six-fold excess of amine.

The starting materials of Formula II may be prepared by reacting a tetrahydronaphthyl di-alcohol of the formula:

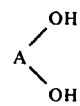   III wherein A is as hereinbefore defined, the position of the hydroxyl groups corresponding to the positions of the ether chains as defined with respect to formula I, with epichlorohydrin. Preferably the reactants are stirred together at moderate or elevated temperature for a long time (mostly some days) under an inert gas atmosphere in the presence of a small amount of a basic catalyst such as an alkai metal hydroxide (e.g. sodium hydroxide), a tertiary amine (e.g. triethylamine) or piperidine. A moderate reaction temperature is preferred when the ether groupings are in ortho position with respect to each other. Advantageously a four- to six fold excess of epichlorohydrin is used. According to another feature of the invention the naphthyl and tetrahydronaphthyl di-ethers of formula I are prepared by reacting a di(glycidyl) ether of the formula:

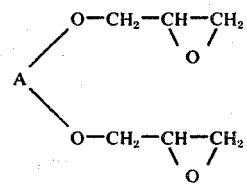   IV wherein A is as hereinbefore defined with an amine of the formula $NH_2R$, wherein R is as hereinbefore defined. Preferred reaction conditions are the same as mentioned above for the reaction of di(chlorohydrin) ether of formula II with an amine of the formula $NH_2R$. The starting materials of formula IV may be prepared by reacting a di(chlorohydrin) ether of formula II with a base in the presence of epichlorohydrin. The reaction may be performed by adding the base to the reaction mixture obtained from the reaction between an aryl di-alcohol of formula III and an excess of epichlorohydrin. Preferably aqueous solutions of alkali metal hydroxides, such as sodium hydroxide, saturated with an alkali metal carbonate, such as sodium carbonate, are used. The reaction is preferably carried out by stirring the reactants at room temperature for several hours, e.g. 1 day. It will be understood that it is also possible to isolate and purify the di(chlorohydrin) ether before reacting it with a base and that the di(glycidyl) ethers may also be obtained by reacting a naphthyl or tetrahydronaphthyl di-alcohol of formula III with epichlorohydrin under the basic conditions needed to obtain a di(glycidyl) ether.

According to another feature of the invention, the naphthyl and tetrahydronaphthyl di-ethers of formula I are prepared by reacting an alkali metal derivative of a naphthyl or tetrahydronaphthyl di-alcohol of formula III with a compound of the formula:

wherein Hal represents a halogen atom, such as chlorine or bromine and R is as hereinbefore defined. The reaction is preferably carried out by heating the reactants in an inert organic solvent such as benzene.

According to another feature of the invention, the naphthyl and tetrahydronaphthyl di-ethers of formula I are prepared by reacting a naphthyl or tetrahydronaphthyl di-alcohol of formula III, or an alkali metal derivative thereof, with a compound of the formula

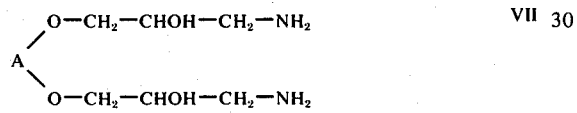

wherein R is as hereinbefore defined. The reaction is preferably carried out by heating the reactants in an inert organic solvent such as benzene. When a naphthyl or tetrahydronaphthyl di-alcohol of formula III is employed as a starting material it is advantageous to add a base, e.g. an alkali metal hydroxide, such as sodium hydroxide. According to another feature of the invention, the naphthyl or tetrahydronaphthyl di-ethers of formula I are prepared by monoalkylating each of the primary groups of a compound of the formula:

$$A\begin{cases} O-CH_2-CHOH-CH_2-NH_2 \\ O-CH_2-CHOH-CH_2-NH_2 \end{cases} \quad VII$$

wherein A is as hereinbefore defined, by methods known per se the alkylation with a radical R (as hereinbefore defined) of primary amines. The alkylation may be carried out by reacting the compound of formula VII with an alkyl halide of the formula Hal—R, wherein Hal and R are as hereinbefore defined, preferably by heating the reactants in an organic solvent, such as ethanol, in the presence of a base, e.g. sodium carbonate. When it is desired to obtain a naphthyl or tetrahydronaphthyl di-ether product of formula I R is an isopropyl group, the alkylation is preferably performed by reacting the compound of formula VII with acetone under reducing conditions. The use of platinum as a catalyst for the reduction with hydrogen is preferred. The reactant acetone may also serve as a solvent medium or a component of a solvent mixture also containing a low boiling alcohol such as methanol. The reaction is preferably carried out at ordinary or slightly elevated temperature.

The starting materials of formula VII may be prepared by reacting a di(glycidyl)ether of the formula IV with ammonia. The reaction is preferably carried out in an organic solvent, such as a lower aliphatic alcohol, e.g. methanol. Reaction temperatures from room temperature upwards can be employed, higher temperatures making it advisable to employ closed vessels wherein pressures surpassing ordinary pressure can be employed.

Acid addition salts of the naphthyl and tetrahydronaphthyl di-ethers of formula I may be prepared by methods known per se. For example, the base may be treated with the equivalent amount of the acid in an inert solvent. Hydrochloric acid is an illustrated acid for this purpose but other acids will work also.

The following Examples illustrate the invention.

EXAMPLE 1

Synthesis of
1,1′-[5,6,7,8-tetrahydro-2,3-naphthalene)dioxy]-bis-[3-(isopropylamino)-propan-2-ol] dihydrochloride 3.45 g. of 2,3-dihydroxy-5,6,7,8-tetrahydronaphthalene, prepared according to J. F. W. McOmie, Tetrah. 24 2289 (1968) are stirred together with 7.77 g. of epichlorohydrin and 0.05 g. of sodium hydroxide dissolved in a few drops of water for 71 hours under a nitrogen atmosphere at 40° C. After cooling 11 ml. of 5N sodium hydroxide, saturated with sodium carbonate, are added and the mixture is stirred vigorously for 24 hours at 20° C. After addition of a small amount of diethyl ether, the layers are separated. The aqueous layer is extracted twice with diethyl ether and the combined ethereal layers are washed three times with water. The solvent and the remaining epichlorohydrin are distilled off and molecular distillation of the residue at $10^{-3}$ mm. Hg yields 4.04 g. of a light yellow oil consisting of crude 1,1′-[(5,6,7,8-tetrahydro-2,3-naphthalene) dioxy]-bis-(2,3-epoxypropane).

This product is heated in a Carius tube for 20 hours at 80° C. in the pre ence of 3 ml. of benzene with a six-fold excess of isopropylamine. The content of the tube is concentrated at reduced pressure and then taken up in 2N acetic acid and washed twice with chloroform. The aminoether is then liberated by adding 2N sodium hydroxide and extracted with chloroform. The chloroform solution is washed three times with water and concentrated by evaporation of the solvent. There are thus obtained 3.42 g. of 1,1′-[(5,6,7,8-tetrahydro-2,3-naphthalene)dioxy]-bis-[3-(isopropylamino)-propan-2-ol] with a purity of 81.2% (determined by titration with hydrochloric acid).

The aminoether is taken up in diethyl ether and converted into the dihydrochloride by adding the calculated amount of an ethereal hydrogen chloride solution. The precipitated salt is filtered off, dried in a desiccator with phosphorus pentoxide and crystallized from anhydrous diethyl ether and absolute ethanol. The melting point of the salt is 86° – 91° C.

EXAMPLE II

Synthesis of
1,1′-(naphthalene-2,3-dioxy)-bis-[3-(isopropylamino)-propan-2-ol]dihydrochloride 16.0 g. of 2,3-dihydroxynaphthalene, 37.0 g. of epichlorohydrin and 12 ml. of absolute ethanol are stirred under a nitrogen atmosphere until the dihydroxynaphthalene is dissolved. Subsequently 0.2 g. of sodium hydroxide, dissolved in a few drops of water, are added and the reaction mixture is stirred for 54 hours at 40° C. The excess of eipchlorohydrin is distilled off under reduced pressure. The resulting oil is dissolved in chloroform, washed twice with water and purified by molecular distillation at $10^{-3}$ mmHg. 28.25 g. of impure 1,1′-(naphthalene-2,3-dioxy)-bis-(3,-chloropropan-2-ol) are obtained.

27 g. of the product are dissolved in 50 ml. of epichlorohydrin and vigorously stirred for 20 hours at room temperature with 46 ml. of a 5N sodium hydroxide solution which is saturated with sodium carbonate. Then diethyl ether is added to the mixture and the layers are separated. The aqueous layer is extracted twice with diethyl ether and the combined ethereal solutions are washed thrice with water. The solvent is then distilled off under reduced pressure. The residue consists of 20.9 g. of impure 1,1'-(naphthalene-2,3-dioxy)-bis-(2,3-epoxypropane) that rather rapidly solidifies. After crystallization from diethyl ethyl 17.5 g. of the pure compound is obtained. Yield 66.3% (calculated from dihydroxynaphthalene); melting point 83.5° - 87.5° C. The diglycidyl ether is reacted with isopropylamine and the reaction product worked up in the same manner as described in Example 1 to give 1,1'-(naphthalene-2,3-dioxy)-bis-[3-(isopropylamine)-propan-2-ol] in a yield of 87.3%.

The base is dissolved in diethyl ether and converted into its dihydrochloride by addition of a calculated amount of etheral hydrogen chloride solution. The melting point of the salt after crystallization from anhydrous acetone and absolute ethanol is 198° – 202° C.

EXAMPLE III

Synthesis of 1,1'-(naphthalene-1,8-dioxy-bis-[3-(isopropylamine) propan-2-ol]dihydrochloride 10.16 g. of 1,8-dihydroxynaphthalene are dissolved under a nitrogen atmosphere in 35.5 g. of epichlorohydrin and the temperature is then raised to 80° C. After that a solution of 5.08 g. of sodium hydroxide in 10 ml. of water is added dropwise with stirring over the course of 6 hours. (the addition is carried out extremely slowly to avoid an excess of hydroxyl ions in the reaction mixture).

The reaction mixture is then stirred for 16 hours at 80° C. and for 24 hours at 100° C. After cooling, chloroform is added and the solution is washed with water until it is neutral. The solvent is evaporated. The residue is submitted to molecular distillation, which yield 10.65 g. of impure 1,1'-(naphthalene-1,8-dioxy)-bis-(2,3-epoxypropane). This product is converted into the isopropylamino compound as indicated in Example 1. There are obtained 4.2 g. of an oil consisting of 1,1'-(naphthalene-1,8-dioxy)-bis-[3-(isopropylamino)-propan-2-ol] with a purity of 85.3%.

The base is dissolved in diethyl ether and converted into the dihydrochloride by addition of a calculated amount of an ethereal hydrogen chloride solution. After crystallization from diethyl ether and ethanol, and subsequently from ethanol, the salt melts at 10° – 106° C.

EXAMPLE IV

Synthesis of 1,1'-(naphthalene-1,2-dioxy)-bis [3-(isopropylamino)-propan-2-ol] dihydrochloride 12.62 g of 1,2-dihydroxynaphthalene, 43.7 g of epichlorohydrin and 0.13 g of sodium hydroxide, dissolved in a few drops of water, are stirred together for 135 hours at 40° C under a nitrogen atmosphere. After cooling to 20° C. 35 ml 5N sodium hydroxide, saturated with sodium carbonate are added and the reaction mixture is stirred vigorously for 24 hours. The layers are separated and the aqueous layer is extracted twice with chloroform. The extracts are added to the organic layer and the combined organic layers are concentrated by evaporation of solvent under reduced pressure. Molecular distillation at 10–3 mm Hg yields 19.72 g of impure 1,1'-(naphthalene-1,2-dioxy)-bis-(2,3-epoxypropane). 13.09 g. of this product are heated for 16 hours at 80° C in a Carius tube with 36 ml of isopropylamine and 13 ml of benzene. After evaporation of the solvent the oily residue is taken up in 2N acetic acid and washed four times with chloroform. The aminoether is then liberated by addition of sodium hydroxide and extraction with chloroform. The solution is washed with water and the solvent is distilled off under reduced pressure. The residue consists of 1,1'-(naphthalene-1,2-dioxy)-bis-[3-(isopropylamino)-propan-2-ol] with a purity of 82.9%. The impure compound is taken up in a mixture of chloroform and diethyl ether and an equivalent amount of hydrogen chloride in diethyl ether is added. The dihydrochloride is crystallized several times from a mixture of anhydrous diethyl ether and absolute ethanol. The melting point is 131°–133° C.

EXAMPLE V

Synthesis of 1,1'-(3-methyl-1,2-naphthalene-dioxy)-bis-[3-isopropylamino)-propan-2-ol]

In a manner similar to that described in the preceding examples various derivatives wherein the naphthalene ring is substituted with other substituents besides the ether chains can be prepared by selection of the proper substituted dihydroxynaphthalene.

For example, by replacement of the 1,2 dihydroxynaphthalene reactant of Example IV with an equivalent amount of the starting material 3-methyl-1,2-dihydroxynaphthalene, a product which comprises a 1,1'-(3-methyl-1,2-naphthalenedioxy)-bis-[3-(isopropylamino)-propan-2-ol] is obtained.

If instead of a 3-methyl substitute compound as final product one wishes to obtain one of the other substituted analogs claimed he need only select a proper starting material such as the following substituted dihydroxynaphthalanes:

4 - methyl - 1,2 - dihydroxynaphthalene
5 - methyl - 1,2 -dihydroxynaphthalene
4 - benzyl - 1,2 - dihydroxynaphthalene
6 - methyl - 2,3 - dihydroxynaphthalene
6,7 - dimethyl - 2,3 - dihydroxynaphthalene
3 - chloro - 1,2 - dihydroxynaphthalene
3 - bromo - 1,2 - dihydroxynaphthalene
6 - bromo - 1,2 - dihydroxynaphthalene
3,4 - dichloro - 1,2 - dihydroxynaphthalene
3 - chloro - 5 - bromo - 1,2 - dihydroxynaphthalene
3,6 - dibromo - 1,2 - dihydroxynaphthalene
1,4 - dichloro - 2,3 - dihydroxynaphthalene
1,4 - dibromo - 2,3 - dihydroxynaphthalene
6,7 - dibromo - 2,3 - dihydroxynaphthalene
4 - methyl - 1 - chloro - 7 - bromo - 2,3 - dihydroxynaphthalene
3,4,6 - tribromo - 1,2 - dihydroxynaphthalene
3,5,6 - tribromo - 1,2 - dihydroxynaphthalene
3 - nitro - 1,2 - dihydroxynaphthalene
2,4 - dinitro - 1,8 - dihydroxynaphthalene
4,5 - dinitro - 1,8 -dihydroxynaphthalene

EXAMPLE VI

Synthesis of 1,1'-[(5,6,7,8-tetrahydro-1,2-naphthalene)dioxyl-]-bis-[3-(isopropylamino)-propan-2-ol]

In the manner as taught in Example I above, by replacement of the 2,3-dihydroxy-5,6,7,8-tetrahydronaphthalene starting material of that example with an equivalent amount of the known compound 1,2-dihydroxy-5,6,7,8-tetrahydronaphthalene, 1,1'-[(5,6,7,8-tetrahydro-1,2-naphthalene)dioxy]-bis-[3-(isopropylamino)-propan-2-ol] is obtained.

Similarly, by starting from appropriate, easily synthesized, substituted 1,2-dihydroxy- and 2,3-dihydroxy-5,6,7,8-tetrahydronaphthalene derivatives, the corresponding 1,1'-[(5,6,7,8-tetrahydronaphthalene)dioxy]-bis-[3-(isopropylamino)-propan-2-ol] derivatives are obtained.

EXAMPLE VII

Synthesis of
1,1'-(naphthalene-2,3-dioxy)-bis-[3-(tert.butylamino)-propan-2-ol]dihydrochloride A mixture of 7.1 g. (26 mmole) of 1,1'-(naphthalene-2,3-dioxy)-bis-(2,3-epoxypropane), 31 g (0.4 mole) of tert.-butylamine and 20 ml of toluene was refluxed with stirring for 60 hours at 80° C. The reaction mixture was concentrated by evaporation of solvent, the residue was taken up in 2 N acetic acid and washed twice with chloroform. The aminoether was then liberated by adding 2 N sodium hydroxide and extracted with chloroform. The chloroform solution was washed three times with water and concentrated by evaporation of the solvent. There was thus obtained 1,1'-(Naphthalene-2,3-dioxy)-bis-[3-(tert.-butylamino)propan-2-ol].

The base was twice crystallised from petroleum ether (boiling range 100°–140° C). Melting point 121°–122° C. The purified compound was dissolved in chloroform and an excess of diethyl ether saturated with hydrogenn chloride gas was added to the solution. Addition of more diethyl ether made the desired dihydrochloride precipitate. The precipitate was filtered off, boiled with a small amount of acetone and, after cooling, filtered off again. The melting point was 162°–168° C.

EXAMPLE VIII

Synthesis of
1,1'-(3-methyl-1,2-naphthalene-dioxy)-bis-[3-(tert.-butylamino)-propan-2-ol]

In a manner similar to that described in Example VII various derivatives wherein the ether chains are in the 1,2- or 1,8-positions and/or the naphthalene ring is substituted with other substituents besides the ether chains can be prepared by selection of the proper substituted or unsubstituted 1,1'-(naphthalenedioxy)-bis-(2,3-epoxypropane). Said starting materials can be obtained from the corresponding dihydroxynaphthalenes by the method described in Example I.

For example, by starting from 3-methyl-1,2-dihydroxynaphthalene a product which comprises 1,1'-(3-methyl-1,2-naphthalenedioxy)-bis-[3-(tert.-butylamino)-propane-2-ol] is obtained.

Similarly, by starting from 1,2-dihydroxynaphthalene, 1,8-dihydroxynaphthalene or the substituted dihydroxynaphthalenes listed in Example V, the corresponding 1,1'-(naphthalene-dioxy)-bis-[3-(tert.-butylamino)-propan-2-ol] compounds are obtained.

In a similar way, by using 1,2-dihydroxy- or 2,3-dihydroxy-5,6,7,8-tetrahydronaphthalene or appropriate, easily synthesized, substituted 1,2-dihydroxy- and 2,3-dihydroxy-5,6,7,8-tetrahydronaphthalene derivatives, the corresponding 1,1'-[(5,6,7,8-tetrahydronaphthalene)dioxy]-bis-[3-(tert.-butylamino)-propan-2-ol] derivatives are obtained.

The invention includes within its scope pharmaceutical preparations containing as an active ingredient at least one of the therapeutically active compounds of the general formula I described above in a daily dose range of from about 5 to 100 mg, adjusted to body weight and clinical indications, in combination with a conventional pharmaceutically acceptable carrier such as lactose if an oral dosage unit such as a tablet, pill or capsule is to be manufactured.

These therapeutically active compositions include the bases themselves or non toxic acid addition salts thereof in admixture with a pharmacologically acceptable carrier suitable for administration to mammals including man. While the pharmaceutical preparations may take any one of the dosage forms customarily employed for administration of therapeutically active substances to animals the preferred dose units are those adopted for oral administration such as tablets, capsules, pills or troches.

These oral dosage forms may be formulated in the known manner with one or more pharmacologically acceptable diluents or excipients such as lactose or starch for example. They may also include materials of a lubricating nature such as non toxic metal salts of higher fatty acid such as the well known calcium stearate. If capsules are to be employed to carry the oral dose absorbable materials such as gelatin be used to contain the active ingredient alone or in admixture with a solid or liquid diluent or carrier.

Liquid preparations which contain the active ingredient may be made in the form of a suspension, emulsion, syrup or elixir of the active substance in water, gylcerine, liquid paraffin or other known and commonly used liquid mediums for preparing liquid orally acceptable pharmaceutical formulations. Dosage forms containing the active ingredient in a form suitable for parenteral administration e.g. as a suspension or emulsion in sterile water, isotonic saline or a suitable organic liquid such as glucose, a vegetable oil such as olive oil or a sterile solution in a non toxic organic solvent as usually employed for injectable preparations suitable for use in mammals.

The following Examples illustrate pharmaceutical preparation according to the invention.

EXAMPLE IX 25 g of 1,1'-[(5,6,7,8-tetrahydro-2,3-naphthalene)-dioxy]-bis-[3-(isopropylamino)-propan-2-ol] dihydrochloride, 25 g of Avicel PH 101 (microcrystalline cellulose) and 1 g of Aerosil (highly purified silicon dioxide) are mixed together and gelatin capsules are filled each with 51 mg of the mixture so that each capsule contains 25 mg of active substance.

EXAMPLE X

800 G of lactose and 200 g of maize starch are mixed with 200 ml of 5% maize starch in water. The mixture is granulated, dried at 55° C and sieved through a no. IV sieve (sieve opening 0.7 mm).

1000 G of the granulate are mixed with 100 g of 1,1'-(naphthalene-2,3-dioxy)-bis-[3-(isopropylamino)-propan-2-ol] dihydrochloride and gelatin capsules are filled each with 110 mg of the mixture so that each capsule contains 10 mg of active substance.

What I claim and desire to secure by Letters Patent for:

1. Naphthyl and tetrahydronaphthyl diethers of the formula

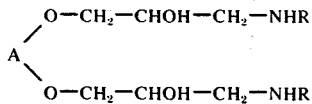

wherein A represents a naphthylene group or a 5,6,7,8-tetrahydronaphthylene group having their ether chains attached to the 1 and 2 or 2 and 3 positions or, when A represents a naphthylene group, to the 1 and 8 positions, which aromatic groups may also have substituted therein one to three substituents selected from halogen atoms, lower alkyl, lower alkenyl, benzyl, nitro and lower acyl groups, said substituents being present in the aromatic part in case A represents a 5,6,7,8-tetrahydronaphthylene group and R represents an isopropyl or tertiary butyl group, and acid addition salts thereof.

2. Naphthyl and tetrahydronaphthyl derivatives according to claim 1, wherein the group A is unsubstituted.

3. A diether according to claim 1, selected from the group consisting of 1,1'-[(5,6,7,8-tetrahydro-2,3-naphthylene)-dioxy]-bis-[3-(isopropylamine)-2-propanol] and its acid addition salts.

4. A diether according to claim 1, selected from the group consisting of 1,1'-(2,3-naphthylenedioxy)-bis-[3-(isopropylamino)-2-propanol] and its acid addition salts.

5. A diether according to claim 1, selected from the group consisting of 1,1'-(1,8-naphthylenedioxy)-bis-[3-(isopropylamino)-2-propanol] and its acid addition salts.

6. A diether according to claim 1, selected from the group consisting of 1,1'-(naphthalene-1,2-dioxy)-bis-[3-(isopropylamino)-2-propanol] and its acid addition salts.

7. A diether according to claim 1, selected from the group consisting of 1,1'-(naphthalene-2,3-dioxy)-bis-[3-(tert.-butylamino)-2-propanol] and its acid addition salts.

8. A diether according to claim 1 which is the compound 1,1'-[(5,6,7,8-tetrahydro-2,3-naphthylene)dioxy]-bis-[3-(isopropylamino)-2-propanol] dihydrochloride.

9. A diether according to claim 1 which is the compound 1,1'-(2,3-naphthylenedioxy)-bis-[3-(isopropylamino)-2-propanol] dihydrochloride.

10. A diether according to claim 1 which is the compound 1,1'-(naphthalene-1,2-dioxy)-bis-[3-(isopropylamino)-2-propanol] dihydrochloride.

11. A diether according to claim 1 which is the compound 1,1'-(naphthalene-2,3-dioxy)-bis-[3-(tert.butylamino)-2-propanol] dihydrochloride.

* * * * *